(12) United States Patent
Feinstein

(10) Patent No.: US 10,493,272 B1
(45) Date of Patent: Dec. 3, 2019

(54) INFERENTIAL ELECTRICAL STIMULATION DEVICE WITH TARGETING CAPABILITIES

(71) Applicant: Feinstein Patents, LLC, Wilkes-Barre, PA (US)

(72) Inventor: Peter A. Feinstein, Palm Beach Gardens, FL (US)

(73) Assignee: Feinstein Patents, LLC, Wilkes-Barre, PA (US)

( * ) Notice: Subject to any disclaimer, the term of this patent is extended or adjusted under 35 U.S.C. 154(b) by 0 days.

(21) Appl. No.: 15/995,872

(22) Filed: Jun. 1, 2018

(51) Int. Cl.
*A61N 1/36* (2006.01)
*A61N 1/32* (2006.01)
*A61N 1/04* (2006.01)

(52) U.S. Cl.
CPC ......... *A61N 1/36021* (2013.01); *A61N 1/323* (2013.01); *A61N 1/36034* (2017.08); *A61N 1/36146* (2013.01); *A61N 1/0408* (2013.01); *A61N 1/36132* (2013.01)

(58) Field of Classification Search
CPC ... A61B 5/4836; A61B 5/0245; A61B 5/7275; A61N 1/0456; A61N 1/08; A61N 1/36; A61N 1/36031; A61N 1/36034
See application file for complete search history.

(56) References Cited

U.S. PATENT DOCUMENTS

| | | |
|---|---|---|
| 7,483,738 B2 | 1/2009 | Tamarkin et al. |
| 7,660,636 B2 | 2/2010 | Castel et al. |
| 8,043,234 B2 | 10/2011 | Talish et al. |
| 8,660,651 B2 | 2/2014 | Castel et al. |
| 9,878,154 B2 | 1/2018 | Tai |

(Continued)

FOREIGN PATENT DOCUMENTS

WO  WO2017172487  10/2017

OTHER PUBLICATIONS

CMS, "Decision Memo for Transcutaneous Electrical Nerve Stimulation for Chronic Low Back Pain (CAG-00429N)", Retrieved on Apr. 26, 2018: https://www.cms.gov/medicare-coverage-database/shared/handlers/highwire.ashx?url=https://www.cms.gov/medicare-coverage-database/details/nca-decisionmemo.aspx@@@NCAld$$$256&session=nuzoqw55m01rmt55tiega4z3&kq=1811865561.

(Continued)

*Primary Examiner* — Deborah L Malamud
(74) *Attorney, Agent, or Firm* — Forge IP, PLLC

(57) ABSTRACT

An interferential current system for performing a therapeutic procedure includes a controller, a stimulation power supply and at least one sensor providing patient derived sensor feedback to the controller. The system also includes at least two electrodes disposed on an epidermis of the patient and arranged to supply transcutaneous electrical impulses to a therapeutic target area when supplied power by the stimulation power supply. The electrodes supply impulses at two different frequencies, giving rise to at least one beat impulse having an interference frequency. The controller generates a patient specific model based at least in part on the sensor feedback, the patient specific model indicative of at least one of: electrode placement appropriate for the transcutaneous electrical impulses to reach the therapeutic target area, appropriate magnitudes of the at least two different frequencies, appropriate magnitude of the interference frequency, and appropriate sweep frequencies.

15 Claims, 4 Drawing Sheets

(56) References Cited

U.S. PATENT DOCUMENTS

| | | |
|---|---|---|
| 2003/0199945 A1 | 10/2003 | Ciulla |
| 2004/0073269 A1 | 4/2004 | Carroll et al. |
| 2008/0208287 A1 | 8/2008 | Palermo et al. |
| 2016/0339239 A1* | 11/2016 | Yoo .................... A61N 1/36107 |
| 2017/0216594 A1 | 8/2017 | Grossman et al. |
| 2017/0259069 A1 | 9/2017 | Baru et al. |
| 2017/0361091 A1 | 12/2017 | Tai |

OTHER PUBLICATIONS

Physical Therapy Web. "Interferential Current (IFC) Equipment", Retrieved on Apr. 26, 2018: http://physicaltherapyweb.com/interferential-current-ifc-equipment.

OTC Wholesale, "Interferential Stimulators IF Units", Retrieved on Apr. 26, 2018: https://www.otcwholesale.com/interferential-stimulators.html.

\* cited by examiner

INFERENTIAL ELECTRICAL STIMULATION DEVICE WITH TARGETING CAPABILITIES

FIELD OF THE INVENTION

The present invention relates to a system and method which employs interferential current (IFC) therapy for a variety of therapeutic purposes, and which also includes targeting capabilities to ensure that the stimulating currents are directed to the appropriate areas of the body to achieve the desired results.

BACKGROUND OF THE INVENTION

Various types of electrical stimulation have been known to be used for various therapeutic purposes. For example, one modality that has gained significant popularity is transcutaneous electrical nerve stimulation (TENS). TENS stimulates the generation of a current that flows through leads to electrodes that are placed on specific locations on a patient's skin in order to elicit reactions in sensory and motor nerve fibers, typically to block pain messages along the nerve fibers. As is known, TENS generally employs low-voltage current that is modulated at low frequency (i.e., 125 Hz) in order to elicit the desired response in the nerve fibers directly under the electrodes through which the current flows.

While TENS has proved successful in limited applications (i.e., involving the stimulation of nerve fibers located just under the skin), there are problems associated with using TENS and like modalities in various situations, which has limited the applications in which such electrical stimulating modalities have traditionally been used.

Specifically, it has been found that the lower the stimulation frequency of an electrical current, the greater the resistance to the passage of the current through the skin and other body tissues, leading to potentially significant discomfort being experienced by the patient. The skin's impedance at 50 Hz is approximately 3200 ohms, while at 4000 Hz it is reduced to approximately 40 ohms. The result of applying this latter frequency is that it will pass more easily through the skin and any other tissues before hitting the target tissue or organ. However, it has also been found that medium frequency current (e.g., 4000 Hz) generally does not have the beneficial therapeutic effects as does the much lower frequency currents typically employed by traditional modalities, such as TENS (e.g., 125 Hz).

Interferential current (IFC therapy) is a unique and separate form of electrical therapeutic stimulation that expands the scope and capabilities for medical intervention in situations not amenable to TENS or any other form of electrical therapy. In general, IFC therapy utilizes two or more medium frequency currents which pass through body tissues simultaneously. They are set up so that their paths cross; and in simple terms they interfere with each other (hence the name "interferential" current therapy). This interference gives rise to an interference or beat frequency, which has the characteristics of low-frequency stimulation. The exact frequency of the resultant beat frequency can be controlled by the input frequencies. For example, if one current is at about 4000 Hz and the other current is at about 3900 Hz, the resultant beat frequency would be at about 100 Hz.

Thus, the basic principle of IFC therapy is to utilize the strong physiological effects of the low frequency electrical stimulation of muscle and nerve tissues at sufficient depth, without the associated painful and somewhat unpleasant side effects of such low frequency stimulation. The medium frequency currents penetrate the tissues with very little resistance, whereas the resulting interference current (low frequency) is in the range that allows effective stimulation of the biological tissues. The resistance (impedance) of the skin is inversely proportional to the frequency of the stimulating current. Thus, the therapeutic beat frequency of IFC results in the desired physiologic response from the target organ or tissue, while requiring less electrical energy input to the deeper tissues than would be required if a single low frequency current was employed, giving rise to less discomfort.

However, the use of IFC is not without its problems. As discussed previously, when using TENS or the like low frequency therapies to treat relatively superficial nerves/tissues, correct placement of the electrodes immediately over the area to be treated is a relatively simple matter. However, being that the use of IFC allows for substantially deeper areas to be treated, and also being that IFC requires that multiple medium frequency currents intersect at the precise area to be stimulated (referred to herein as the "therapeutic target area"), targeting of the anatomic area to be affected becomes a required component of the use of IFC treatment, rather than simply putting electrodes on the skin to treat a localized area of pain and discomfort. Heretofore, there is no known system employing IFC which also adequately ensures that the stimulating currents are appropriately targeted such that they intersect to generate the correct beat frequency precisely at the therapeutic target area.

Therefore, what is desired is a system and method employing electrical stimulation for therapeutic purposes, which allows for deep penetration of an appropriate low frequency current but without causing tissue damage and/or patient discomfort and which ensures that the therapeutic low frequency currents are accurately directed to the desired therapeutic target area.

SUMMARY OF THE INVENTION

In one respect, the present invention is directed to an interferential current system for performing a therapeutic procedure on a patient, the device including a controller, a stimulation power supply in communication with the controller and at least one sensor providing sensor feedback to the controller, the sensor feedback indicative of a patient parameter derived from the patient. The system also includes at least two electrodes in electrical communication with the stimulation power supply, the electrodes disposed on an epidermis of the patient and arranged to supply transcutaneous electrical impulses to a therapeutic target area when supplied power by the stimulation power supply. The at least two electrodes supply transcutaneous electrical impulses at two different frequencies, the transcutaneous electrical impulses provided at two different frequencies giving rise to at least one beat impulse having an interference frequency. The controller generates a patient specific model based at least in part on the sensor feedback, the patient specific model indicative of at least one of: electrode placement appropriate for the transcutaneous electrical impulses to reach the therapeutic target area, appropriate magnitudes of the at least two different frequencies and an appropriate magnitude of the interference frequency.

In some embodiments, the at least one sensor provides sensor feedback to the controller in real time during the therapeutic procedure. In certain of these embodiments, the controller updates the patient specific model during the therapeutic procedure based at least in part upon the sensor feedback. In certain embodiments, the transcutaneous electrical impulses are adjusted during the therapeutic procedure based at least in part upon the sensor feedback. The certain of these embodiments, the transcutaneous electrical impulses are adjusted automatically and in real time by the controller during the therapeutic procedure based at least in part upon the sensor feedback. The model also incorporates on and off, either manual or automatic, to address target organ tissue and neurologic innervation adaptability that can result in escape from the effects of a particular frequency so that adjusting wave forms and frequencies at different time periods prevents target organ escape from response.

In some embodiments, the controller generates a computer assisted plan at least in part based on the patient specific model, and the controller activates the stimulation power supply based at least in part upon the computer assisted plan. In certain of these embodiments, the controller updates the computer assisted plan during the therapeutic procedure based at least in part upon the sensor feedback.

In some embodiments, the at least one sensor comprises an imaging sensor, and the sensor feedback comprises image data indicative of patient anatomy. In certain of these embodiments, the at least one sensor comprises an imaging sensor employing at least one of the following modalities: ultrasound, Level II ultrasound, 3D ultrasound, 4D ultrasound, trans esophageal echogram (TEE), x-rays, computed tomography (CT) scanning, magnetic resonance imaging (MRI) scanning, 3D magnetic resonance imaging (MRI) scanning, positron emission tomography (PET), radiography, elastography, plethsmethography, thermography, bone scanning and image intensification. In certain embodiments, the at least one sensor comprises at least two of any combination of imaging sensors employing at least two of the following modalities: ultrasound, Level II ultrasound, 3D ultrasound, 4D ultrasound, trans esophageal echogram (TEE), x-rays, computed tomography (CT) scanning, magnetic resonance imaging (MRI) scanning, 3D magnetic resonance imaging (MRI) scanning, positron emission tomography (PET), radiography, elastography, plethsmethography, thermography, bone scanning and image intensification.

In some embodiments, the at least one sensor comprises an electrical sensor, and the sensor feedback comprises electrical signal data. In certain of these embodiments, the at least one sensor comprises an electrical sensor employing at least one of the following modalities: electroencephalography (EEG), echocardiography (EKG), nerve conduction tests and electromyograms (NCT and NCV) and somatosensory evoked potentials (SSEP). In some embodiments, the at least one sensor is integrated with a robotics device, machine, or algorithm and/or with a mobile device.

In some embodiments, the plurality of electrodes comprises: a first electrode supplying transcutaneous electrical impulses at a first frequency and a second electrode supplying transcutaneous electrical impulses at a second frequency different than the first frequency, the transcutaneous electrical impulses provided at the first and second frequencies giving rise to a first beat impulse having a first interference frequency; and, a third electrode supplying transcutaneous electrical impulses at a third frequency and a fourth electrode supplying transcutaneous electrical impulses at a fourth frequency different than the third frequency, the transcutaneous electrical impulses provided at the third and fourth frequencies giving rise to a second beat impulse having a second interference frequency.

In accordance with another aspect of the present invention, an interferential current system for performing a therapeutic procedure on a patient includes a controller, a stimulation power supply in communication with the controller and at least one sensor providing sensor feedback to the controller, the sensor feedback indicative of a patient parameter derived from the patient, wherein the at least one sensor provides sensor feedback to the controller in real time during the therapeutic procedure. The system also includes a plurality of electrodes in electrical communication with the stimulation power supply, the plurality of electrodes disposed on an epidermis of the patient and arranged to supply transcutaneous electrical impulses to a therapeutic target area when supplied power by the stimulation power supply. The plurality of electrodes comprises at least two electrodes supplying transcutaneous electrical impulses at two different frequencies, the transcutaneous electrical impulses provided at two different frequencies giving rise to at least one beat impulse having an interference frequency. The transcutaneous electrical impulses are adjusted automatically and in real time by the controller during the therapeutic procedure based at least in part upon the sensor feedback. The controller generates a patient specific model based at least in part on the sensor feedback, the patient specific model indicative of at least one of: electrode placement appropriate for the transcutaneous electrical impulses to reach the therapeutic target area, appropriate magnitudes of the at least two different frequencies and an appropriate magnitude of the interference frequency. The controller updates the patient specific model during the therapeutic procedure based at least in part upon the sensor feedback and such other data accumulated over the course of use in all patients where the system has been used to optimize targeting based on "big data" accumulation and analysis.

In accordance with still another aspect of the present invention, an interferential current system for performing a therapeutic procedure on a patient includes a controller, a stimulation power supply in communication with the controller and at least two or multiple sensors providing sensor feedback to the controller, the sensor feedback indicative patient parameters derived from the patient. The at least two or multiple sensors employ at least two of the following modalities: ultrasound, Level II ultrasound, 3D ultrasound, 4D ultrasound, trans esophageal echogram (TEE), x-rays, computed tomography (CT) scanning, magnetic resonance imaging (MRI) scanning, 3D magnetic resonance imaging (MRI) scanning, positron emission tomography (PET), radiography, elastography, plethsmethography, thermography, bone scanning, image intensification, electroencephalography (EEG), echocardiography (EKG), nerve conduction tests and electromyograms (NCT and NCV) and somatosensory evoked potentials (SSEP). The system also includes a plurality of electrodes in electrical communication with the stimulation power supply, the plurality of electrodes disposed on an epidermis of the patient and arranged to supply transcutaneous electrical impulses to a therapeutic target area when supplied power by the stimulation power supply. The plurality of electrodes comprises at least two electrodes supplying transcutaneous electrical impulses at two different frequencies, the transcutaneous electrical impulses provided at two different frequencies giving rise to at least one beat impulse having an interference frequency. The controller generates a patient specific model based at least in part on the sensor feedback, the patient specific model indicative of at least one of: electrode placement appropriate for the transcutaneous electrical impulses to reach the therapeutic target area, appropriate magnitudes of the at least two different frequencies and an appropriate magnitude of the interference frequency.

The embodiments as discussed above are illustrative and are not intended to exhaust all possible arrangements, modifications, and variations of features of the invention.

DETAILED DESCRIPTION OF THE INVENTION

Figure 1:
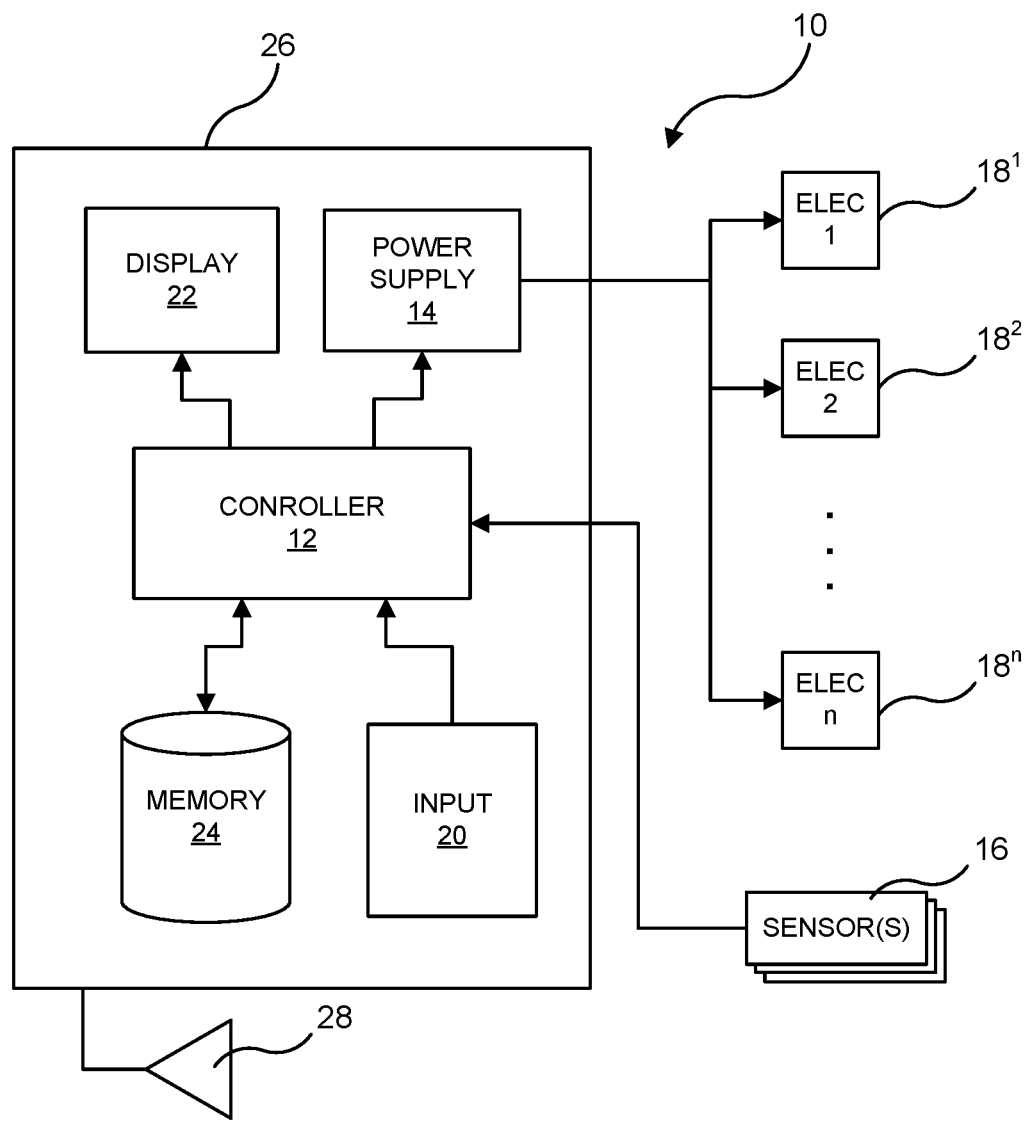
FIG. 1 is a block diagram schematically illustrating a basic device employing interferential current (IFC) therapy together with targeting capabilities to ensure that the stimulating currents are directed to the appropriate areas of the body to achieve the desired results, according to an exemplary embodiment of the present invention.

Referring now to the Figures and first to FIG. 1, there is shown an exemplary embodiment of a device (10) for performing various therapeutic treatments on a patient (50). The device (10) includes a controller (12), a stimulation power supply (14) in communication with the controller (12) and one or more sensors (16) providing sensor feedback to the controller (12), The device (10) also includes a plurality of electrodes ($18^1$, $18^2$ ... $18^n$) in electrical communication with the stimulation power supply (14). As will be explained in more detail below, the controller (12), the stimulation power supply (14) and the electrodes ($18^1$, $18^2$ ... $18^n$) are particularly configured to employ interferential current (IFC) therapy, while the controller (12) and the one or more sensors (16) are configured to provide targeting capabilities to ensure that the stimulating currents are directed to the appropriate areas of the patient's body to achieve the desired results.

The plurality of electrodes ($18^1$, $18^2$ ... $18^n$) are disposed on an epidermis (52) of the patient (50) and are arranged to supply transcutaneous electrical impulses that cause a variety of reactions, depending upon the targeted area, as explained in more detail below. Various options are possible for electrode ($18^1$, $18^2$ ... $18^n$) placement, as well as types of electrodes used, also as is explained in more detail below.

The controller (12) causes the stimulation power supply (14) to supply power to the plurality of electrodes ($18^1$, $18^2$ ... $18^n$) according to a programmed set of parameters, again depending on the targeted area and the desired response to be elicited.

The device (10) also includes an input mechanism (20) (such as a keyboard, touchscreen, joystick or the like) as is known in the art, which allows the user to enter control parameters and the like. As but one example, input mechanism (20) may include a button or other type of controller to turn the device on or off manually, or to trigger the stimulation power supply (14). This may be particularly desirable, for example, when the device (10) is used in connection with causing certain desired responses intended to be performed on-demand by the patient. Another example allowing greater flexibility and ease of use is based on a mobile device (such as a cellphone) or mobile device (e.g., cellphone) app. Such an app might also have the ability to notify a patient or a healthcare provider that the sensors are accumulating data indicating that at a specific time the user has to activate the IFC device as in an alarm for manual use by the user. Similarly, such a program could automatically turn on the device at a specific time for a specific reason without any input from the person being treated.

Also as is well known in the art, the device (10) includes a display (22) to provide visual and/or auditory output to the patient and/or another user of the device (10) (e.g., a medical professional). The display (22) may also present the patient/user with other helpful information. For example, the device (10) may be linked to a mapping app on a mobile device (such as Google maps or Waze) in order to display or otherwise provide information concerning appropriate healthcare or other public facilities.

In some embodiments the system further includes the ability to transmit information and data obtained via the Internet or other mechanism to remote or off site locations for consultation or expert input, interpretation, and monitoring of data garnered during or after the procedure, or for incorporation into electronic medical records (EMRs), or for telehealth applications.

The device may further include an antenna (28) or the like (such as Bluetooth functionality) in order to provide connectivity to a mobile network or direct connectivity to a mobile phone, computerized fitness tracker, smart watch, etc. The antenna (28) or the like may also be used to provide wireless connectivity for the sensor(s) (16) rather than employing a wired connection.

The device (10) further includes a memory (24), which allows the device to store various parameters that may be employed by the controller (12).

The controller (12), stimulation power supply (14), input mechanism (20), display (22), memory (24) and antenna (28) may be contained in a housing (26), as should be apparent to those skilled in the art. Various types of connectors may be provided on the housing to allow for connection of the electrodes ($18^1$, $18^2$ ... $18^n$), the sensor (16), or various other devices (e.g., mobile phones, tablets, smart watches, etc.) also as should be apparent to those skilled in the art.

As discussed above, the present invention is particularly adapted to employ interferential current (IFC) technology. Also as discussed above IFC therapy generally utilizes two medium frequency currents which pass through the tissues simultaneously. They are set up so that their paths cross; and in simple terms they interfere with each other. This interference gives rise to an interference or beat frequency, which has the characteristics of low-frequency stimulation. The exact frequency of the resultant beat frequency can be controlled by the input frequencies. For example, if one current is at about 4000 Hz and the other current is at about 3900 Hz, the resultant beat frequency would be at about 100 Hz.

Figure 2:
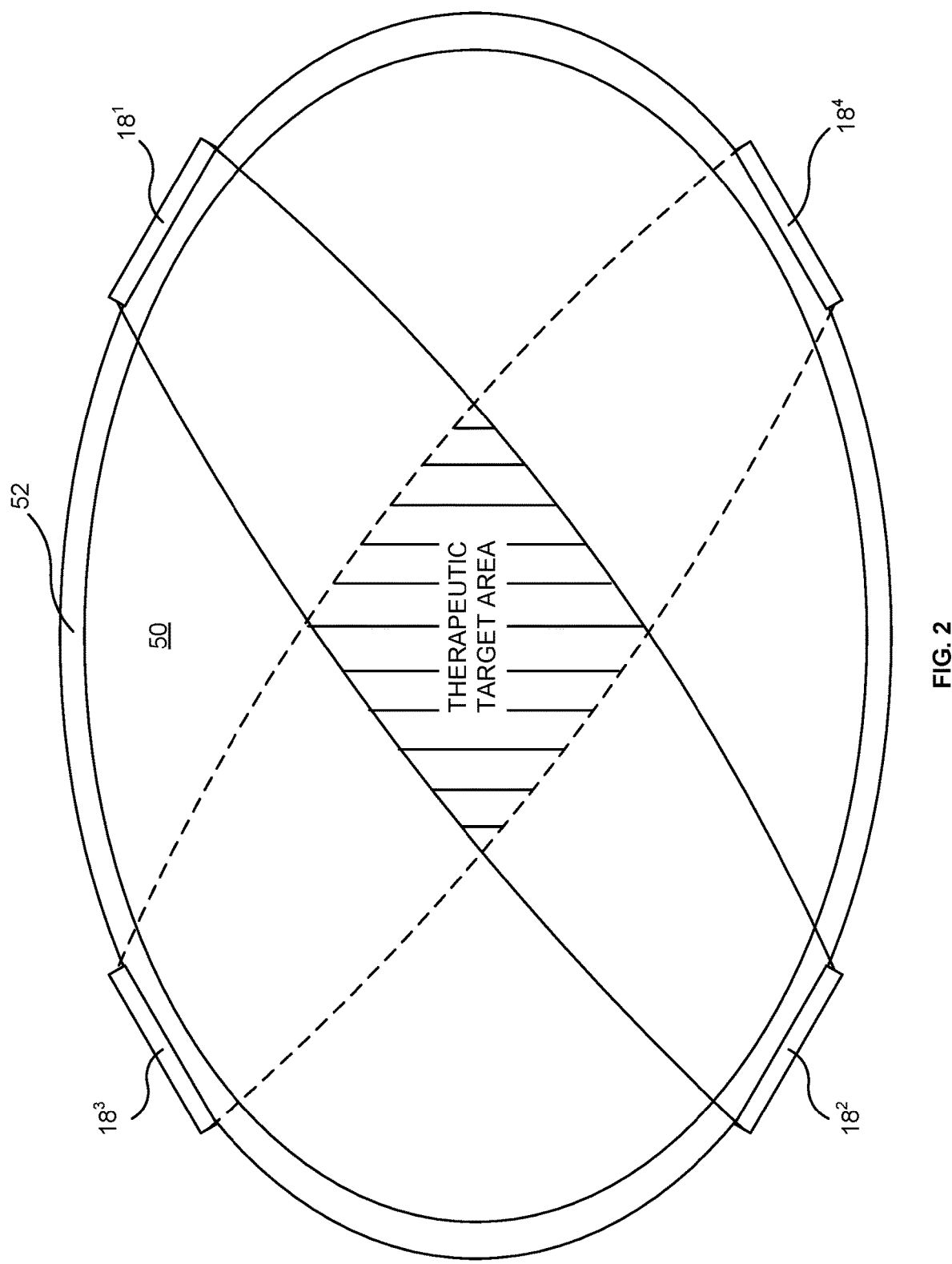
FIG. 2 is schematic view illustrating rudimentary operational characteristics of the device shown in FIG. 1.

Referring now to FIG. 2, an exemplary arrangement of electrodes employing IFC therapy is shown applied to the epidermis (52) of a patient (50). In this example, a first pair of electrodes ($18^1$, $18^2$) supplies transcutaneous electrical impulses at a first frequency (represented by solid lines) and a second pair of electrodes ($18^3$, $18^4$) supplies transcutaneous electrical impulses at a second frequency (represented by dashed lines) different than the first frequency. The transcutaneous electrical impulses provided at the first and second frequencies giving rise to a beat impulse in a therapeutic target area (located at the position shown in FIG. 2 where the area defined by solid lines and the area defined by dashed lines overlap, as highlighted with vertical cross-hatching) having an interference frequency.

The beat impulse is controlled depending on the type of nerve/tissue/organ to be stimulated, as well as on real-time feedback of the elicited response (as explained in more detail below). For example, it has been found that beat impulses having a frequency in the range of from 1-5 Hz may provide desirable stimulation properties for sympathetic nerves, beat impulses having a frequency in the range of from 10-150 Hz may provide desirable stimulation properties for parasympathetic nerves, beat impulses having a frequency in the range of from 10-50 Hz may provide desirable stimulation properties for motor nerves, beat impulses having a frequency in the range of from 90-100 Hz may provide desirable stimulation properties for sensory nerves, beat impulses having a frequency in the range of from 90-150 Hz may provide desirable stimulation properties for nociceptive fibers, and beat impulses having a frequency in the range of from 1-10 Hz may provide desirable stimulation properties for smooth muscle. As will be recognized, other types of nerves/tissues/organs may respond to other beat impulse frequencies.

Figure 3B:
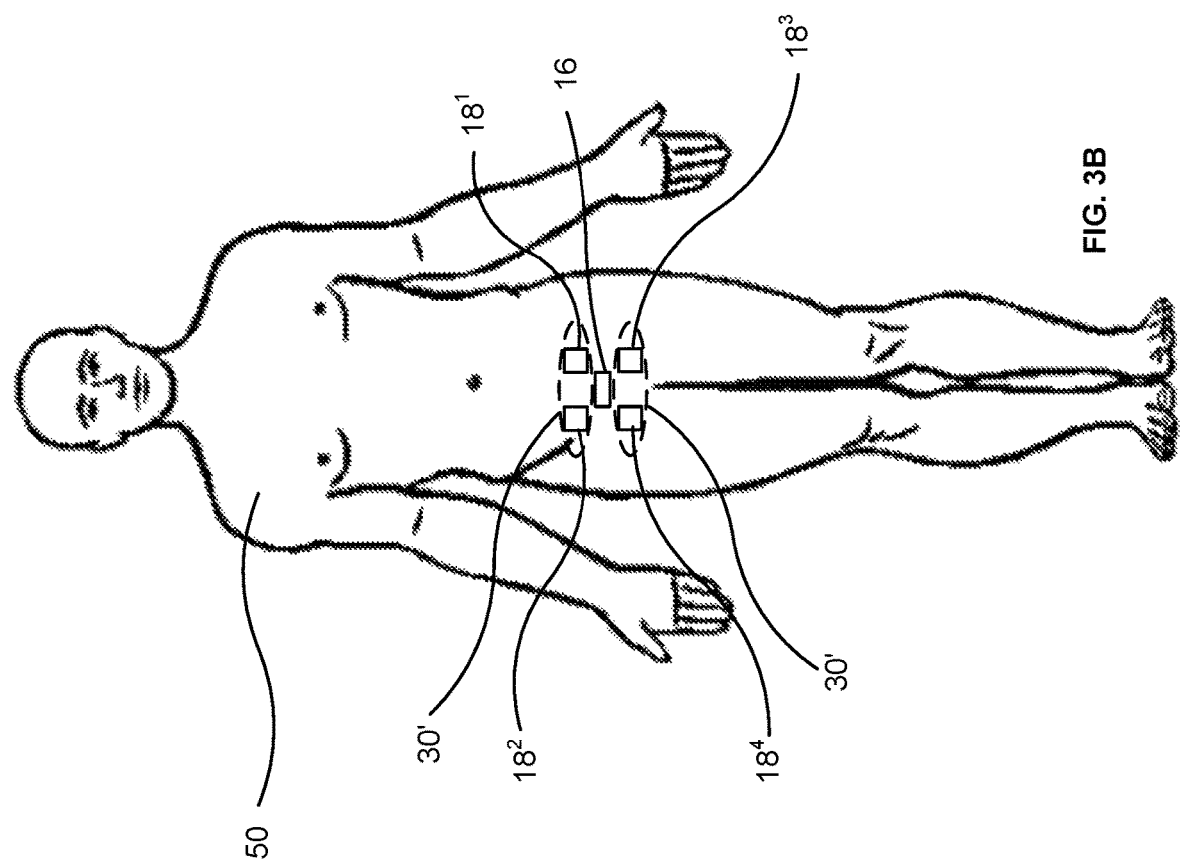
FIGS. 3A and 3B are schematic views illustrating basic exemplary options for the placement on a patient of the electrodes of the device shown in FIG. 1.
Figure 3A:
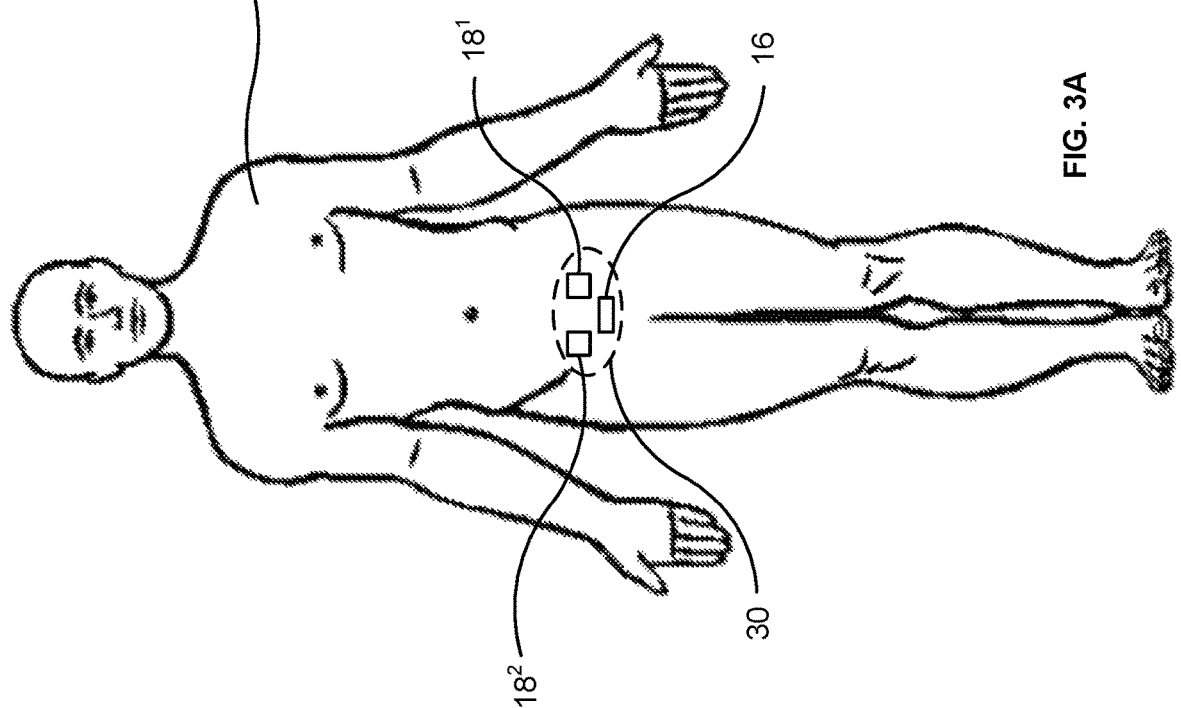

Turning now to FIGS. 3A and 3B, an exemplary positioning of electrodes ($18^1$ and $18^2$) on the patient (50) is shown. In this exemplary embodiment, a first electrode ($18^1$) supplies transcutaneous electrical impulses at a first frequency and a second electrode ($18^2$) supplies transcutaneous electrical impulses at a second frequency different than the first frequency, the transcutaneous electrical impulses provided at the first and second frequencies giving rise to a first beat impulse having a first interference frequency. The first and second electrodes ($18^1$, $18^2$) are positioned such that the therapeutic target area thereof is positioned to cause stimulation of a first desired nerve/tissue/organ with the first beat impulse having the first interference frequency as is explained in more detail below.

With respect specifically to FIG. 3B, a third electrode ($18^3$) supplies transcutaneous electrical impulses at a third frequency and a fourth electrode ($18^4$) supplies transcutaneous electrical impulses at a fourth frequency different than the third frequency, the transcutaneous electrical impulses provided at the third and fourth frequencies giving rise to a second beat impulse having a second interference frequency. The third and fourth electrodes ($18^3$, $18^4$) are positioned such the therapeutic target area thereof is positioned to cause stimulation of a second desired nerve/tissue/organ with the second beat impulse having the second interference frequency as is explained in more detail below.

As will be understood by those skilled in the art, additional pairs of electrodes may be employed to produce additional beat impulses at the same or different beat frequencies as those described above, depending on the particular application of the device (10).

Each of the first pair of electrodes ($18^1$, $18^2$) may be formed as a separate pad, or as illustrated in FIG. 3A, both electrodes ($18^1$, $18^2$) may be disposed on a common pad (30) for ease of placement on the patient (50). In the example of FIG. 3A, the sensor (16) is also disposed on the same pad (30) for further ease of placement.

In the exemplary embodiment of FIG. 3B, both of the first pair of electrodes ($18^1$, $18^2$) are disposed on a common pad (30') and both of the second pair of electrodes ($18^3$, $18^4$) are disposed on another common pad (30') for ease of placement on the patient (50). In the example of FIG. 3B, however, the sensor (16) is disposed separately from the electrode carrying pads (30').

The pads (30, 30") and/or the electrodes (18) may take any of numerous forms. In some cases, the pads/electrodes may be formed with an adhesive on one side, such that the pads/electrodes can be affixed to the patient's skin. If desired, the pads/electrodes can be incorporated into or onto to an article of clothing (e.g., a glove or a sock), a surgical drape or the like, a medical device, such as a splint, cast or other immobilization device, a wheelchair, a hospital bed, etc. The pads/electrodes can also take the form of a thin, flexible electrical circuit, such as in the nature of a temporary tattoo formed of an electrically conductive material.

Figure 4:
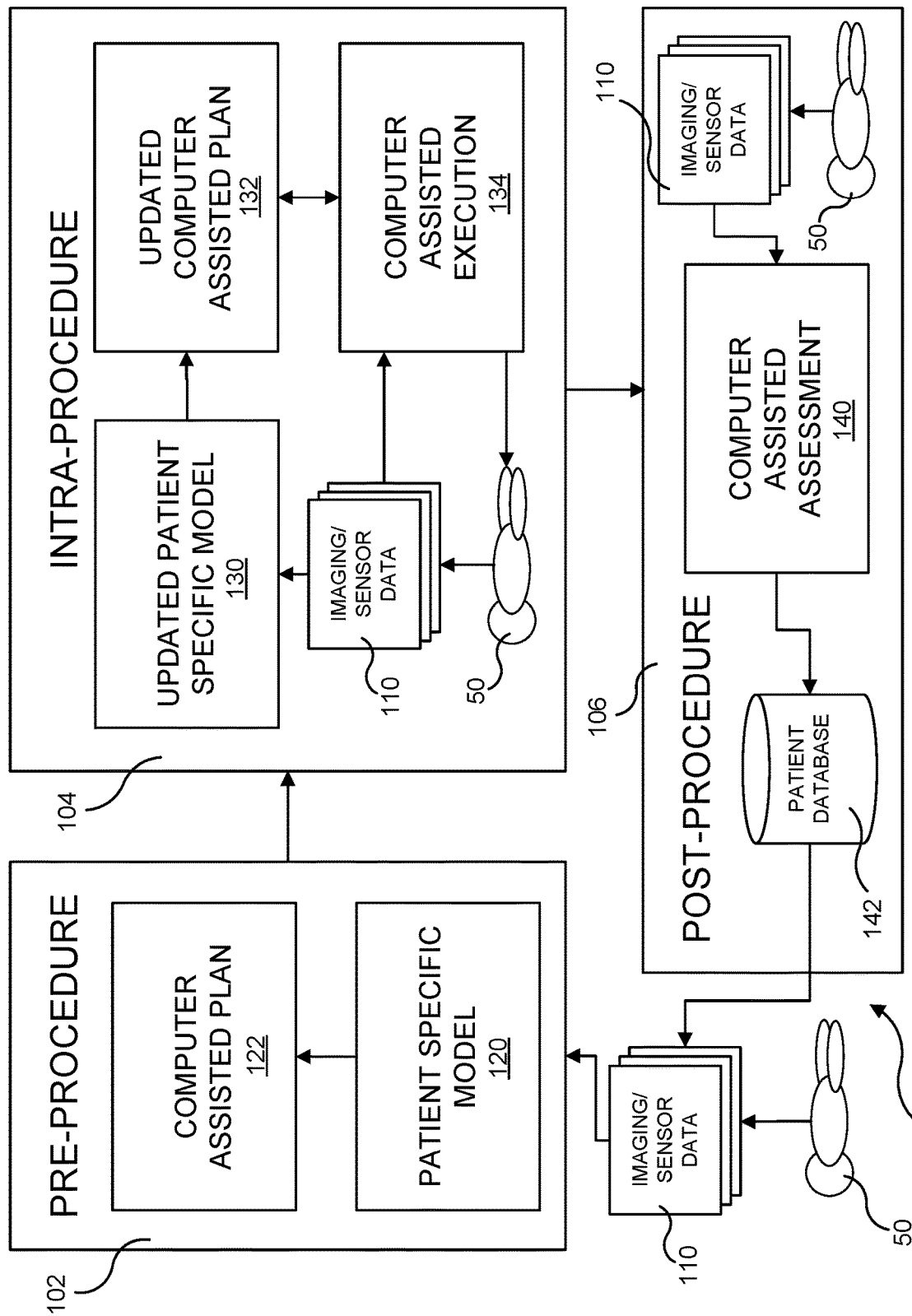
FIG. 4 is a schematic view illustrating an exemplary targeting scheme employed by the device shown in FIG. 1.

Referring now to FIG. 4, a targeting aspect of the present invention is schematically shown. In general, medical procedures are highly interactive processes, and many critical decisions are made during the procedure and executed immediately. The goal of the targeting aspect of the present invention is to provide intelligent, versatile tools that augment the medical professional's ability to treat patients, both prior to and during the procedure.

As can be seen, the targeting system (100) shown in FIG. 4 can be broken down into three main stages: pre-procedure (102), intra-procedure (104) and post-procedure (106). A key aspect of all three stages is imaging/sensor data (110) collected from the patient (50), for example using the one or more sensors (16).

The types of imaging/sensor data (110) can vary greatly, depending on the particular nerves/tissues/organs to be stimulated, and the manner in which they are intended to be stimulated. In this regard, it is contemplated that the device (10) of the present invention can be used in connection with numerous applications involving various biological systems.

For example, device (10) can be used for the purposes of assisting a patient suffering from a condition that inhibits the patient from achieving spontaneous and controlled micturition, as described in more detail in copending U.S. patent application Ser. No. 15/951,318, filed by applicant of the present application. Other examples of contemplated applications for the device (10) according to the present invention include: erectile dysfunction; various cardiac issues (e.g., cardiac arrhythmias, congestive heart failure, cardiomyopathies); various neurological issues (e.g., traumatic brain injury, deep brain stimulation, Parkinson's disease, Alzheimer's disease, concussion, multiple sclerosis, failed back syndrome/arachnoiditis); various OB/GYN issues, including better control of menstrual pain, bleeding and cramps, and inducing and controlling labor; control of bleeding and/or reducing edema, for example during surgery or after a trauma; various gastrointestinal issues (e.g., ileus—post op or having other causes, stimulating a sense of satiety as an alternative to bariatric surgery and gastric banding, bile duct and/or pancreatic duct sphincter control, gall bladder contraction); various orthopedic and musculoskeletal issues (e.g., muscle stimulation for post-op joint replacement rehab, fracture care, sports medicine-athletic injuries, traumatic injury, robotic control utilizing feedback from muscle stimulation, activation and deactivation for mechanical parts such as amputation prostheses and mechanical devices to aide in mobilization of paralysis or spinal cord injuries); and various other conditions that may benefit from IFC therapy.

As will be recognized by those skilled in the art, different types of imaging/sensor data (110) will be relevant for different of the above examples, depending on the particular application in question, with there being many known and yet to be developed diagnostic modalities that may be appropriate.

For example, many imaging modalities are known that would be appropriate to collect imaging sensor data (110), including ultrasound (including Level II ultrasound, 3D ultrasound, 4D ultrasound, etc.), trans esophageal echogram (TEE), x-rays, computed tomography (CT) scanning, magnetic resonance imaging MRI scanning (3D or otherwise), positron emission tomography (PET), radiography, elastography, thermography, bone scanning, etc. More advanced imaging techniques involving combinations of various modalities may also be used, such as MRI-TRUS (magnetic resonance imaging/transrectal ultrasound) fusion, which has been used to perform targeted prostate biopsies.

The imaging modalities used may be static, or dynamic. In addition, various functional modalities may be employed, such as Doppler ultrasound to evaluate blood flow or other forms of plethsmethography (which is measurement of blood flow dynamics) or various functional neuroimaging techniques to evaluate brain activity. Image intensification is another diagnostic modality that can be used, which affords x-ray assessment in real time with motion as in some of the ultrasound options. This can be important during procedures such as cardiac catheterizations.

Additionally, various other types of electrical sensor data may be used to assist with targeting of the IFC currents. For example, electroencephalography (EEG) may be employed for applications involving the brain, while echocardiography (EKG) may be employed for applications involving the heart. Nerve conduction tests and electromyograms (NCT and NCV) and somatosensory evoked potentials (SSEP) may also be employed.

The sensor(s) may be integrated with a robotics device, machine, or algorithm. Examples of this would be surgical robotics machines made by MAKO Surgical, Intuitive Surgical, and Restoration Robotics which respectively are used for surgically-assisted operations in terms of joint replacements, robotic abdominal surgery, robotic placement of hair transplant follicles, and robotic assisted prostate surgery. Rather than using robotics to aid surgeons, the robotics technology can be combined with IFC to give extremely accurate microscopic and larger field targeting through the IFC.

In fact, the robotics could be combined with IFC such that an individual could do essentially "IFC robotic surgery" in which the robotic assisted mechanism not only targets the area through robotic anatomic analysis, but also then the robotic arms controlled by the surgeon would place the appropriate interferential electrodes on the skin and, through the connecting robotic arm also supply the appropriate electric current with feedback through the robotic surgery targeting technology and device.

Instead or in addition, the sensor(s) may be integrated with a cellphone or other mobile device as the coordinating interface. This is envisioned as incorporating current cellphone apps that actually provide handheld diagnostic ultrasounds using either the cellphone camera mechanism or a program using the cellphone's screen. For example, there are cellphone apps currently being used by women to view their fetus at any time during pregnancy as opposed to having an actual formal ultrasound. This type of mobile targeting device could, in the clinical setting, be easier to use than the currently employed bladder scanner ultrasound machine. Using such a cellphone app would include wireless transmission of the electrical impulses to the electrodes, or could even include a transducer connected to wires, which then plug into a port in either a computer or the cellphone, similar to the way music earplugs now transmit music from a cellphone either through wires, or wireless headphones.

It should also be recognized that a combination of two or more of the above described, and/or other, techniques may be employed to collect the imaging/sensor data (110) employed by the targeting system (100).

Turning again to FIG. 4, imaging/sensor data (110) is used in the pre-procedure stage (102) to generate a patient specific model (at 120), such as a three-dimensional model of the patent's anatomy. Of particular importance is locating on the model the one or more therapeutic target areas of the patient to be targeted with the IFC. This model is then used with other data in the memory (24) of device (10) to generate a computer assisted plan (at 122), including the location for initial placement of the electrodes (18), as well as data indicative of the frequencies of the interferential currents to be generated to create the beat impulse(s) having the interference frequency/frequencies desired for the particular application.

The electrodes (18) are positioned according to the computer assisted plan (122), and the IFC therapy procedure may be commenced. During the intra-procedure stage (104), additional imaging/sensor data (110) may continue to be collected from the patient (50), which data (110) may be used to update the patient specific model (at 130), for example, if changes to the patient's anatomy occur, and to update the computer assisted plan (at 132). For example, it may be determined that one or more of the electrodes (18) should be repositioned and/or that the frequencies of the interferential currents require adjustment so that the frequencies of the resulting beat impulse(s) are correspondingly adjusted.

Also, during the intra-procedure stage (104), computer assisted execution of the plan may be performed (at 134), for example, by the controller (12). Such execution may be performed automatically, manually in response to user input or automatically in part and manually in part. For example, the controller (12) may increase and/or decrease the frequencies of the resulting beat impulses automatically in real time in response to sensed conditions. It may also control the robotics previously mentioned, and it would be in communication with those targeting algorithms.

After the procedure is completed, in a post-procedure stage (106), imaging/sensor data (110) may continue to be collected, and then a computer assisted assessment may be performed (at 140) in order to generate data concerning the impact of the procedure on the patient (50). This data, which may be stored in a database (142) may be used in order to help with planning future procedures for the same patient (50) or with other patients, for example who will undergo similar procedures. For example, the data may be helpful in generating the computer assisted plan (122).

The data can be connected to and used with telehealth, electronic medical record (EMR), and offsite doctor transmission and analysis programs as part of the integration with advanced computer algorithms and trends in medical care.

Although the invention has been described with reference to particular arrangement of parts, features, and the like, these are not intended to exhaust all possible arrangements or features, and indeed many modifications and variations will be ascertainable to those of skill in the art.

For example, the present invention is designed so that any imaging/sensor modalities that are available but have not been incorporated into the description of the invention, or that become available as technology advances, are considered part of the invention and incorporated by modifying the electrical and mechanical parts and protocols associated with them to achieve the aims of the present invention.

What is claimed is:

1. An interferential current system for performing a therapeutic procedure on a patient, said device comprising:

a controller;

a stimulation power supply in communication with said controller;

at least one sensor providing sensor feedback to said controller, said sensor feedback indicative of a patient parameter derived from the patient;

a plurality of electrodes in electrical communication with said stimulation power supply, said plurality of electrodes configured to be disposed on an epidermis of the patient and arranged to supply transcutaneous electrical impulses to a therapeutic target area when supplied power by said stimulation power supply, wherein said plurality of electrodes comprises at least two electrodes supplying transcutaneous electrical impulses at two different frequencies, the transcutaneous electrical impulses provided at two different frequencies giving rise to at least one beat impulse having an interference frequency; and wherein said controller generates a patient specific model based at least in part on said sensor feedback, the patient specific model indicative of at least: electrode placement appropriate for the transcutaneous electrical impulses to reach the therapeutic target area, appropriate magnitudes of the at least two different frequencies and an appropriate magnitude of the interference frequency.

2. The interferential current system of claim 1 wherein said at least one sensor provides sensor feedback to said controller in real time during the therapeutic procedure.

3. The interferential current system of claim 2 wherein said controller updates the patient specific model during the therapeutic procedure based at least in part upon the sensor feedback.

4. The interferential current system of claim 2 wherein the transcutaneous electrical impulses are adjusted during the therapeutic procedure based at least in part upon the sensor feedback.

5. The interferential current system of claim 4 wherein the transcutaneous electrical impulses are adjusted automatically and in real time by the controller during the therapeutic procedure based at least in part upon the sensor feedback.

6. The interferential current system of claim 1 wherein the controller generates a computer assisted plan at least in part based on the patient specific model, and wherein the controller activates said stimulation power supply based at least in part upon the computer assisted plan.

7. The interferential current system of claim 6 wherein said controller updates the computer assisted plan during the therapeutic procedure based at least in part upon the sensor feedback.

8. The interferential current system of claim 1, wherein said at least one sensor comprises an imaging sensor, and wherein the sensor feedback comprises image data indicative of patient anatomy.

9. The interferential current system of claim 8, wherein said at least one sensor comprises an imaging sensor employing at least one of the following modalities: ultrasound, Level II ultrasound, 3D ultrasound, 4D ultrasound, trans esophageal echogram (TEE), x-rays, computed tomography (CT) scanning, magnetic resonance imaging (MRI) scanning, 3D magnetic resonance imaging (MRI) scanning, positron emission tomography (PET), radiography, elastography, plethsmethography, thermography, bone scanning and image intensification.

10. The interferential current system of claim 9, wherein said at least one sensor comprises at least two of any combination of imaging sensors employing at least two of the following modalities: ultrasound, Level II ultrasound, 3D ultrasound, 4D ultrasound, trans esophageal echogram (TEE), x-rays, computed tomography (CT) scanning, magnetic resonance imaging (MRI) scanning, 3D magnetic resonance imaging (MRI) scanning, positron emission tomography (PET), radiography, elastography, plethsmethography, thermography, bone scanning and image intensification.

11. The interferential current system of claim 1, wherein said at least one sensor comprises an electrical sensor, and wherein the sensor feedback comprises electrical signal data.

12. The interferential current system of claim 11, wherein said at least one sensor comprises an electrical sensor employing at least one of the following modalities: electroencephalography (EEG), electrocardiogram (EKG), nerve conduction tests and electromyograms (NCT and NCV) and somatosensory evoked potentials (SSEP).

13. The interferential current system of claim 1, wherein said at least one sensor is integrated with a further element selected from the group consisting of a robotics device, a robotics machine, a robotics algorithm, a mobile device and combinations thereof.

14. The interferential current system of claim 1, wherein said plurality of electrodes comprises:

a first electrode supplying transcutaneous electrical impulses at a first frequency and a second electrode supplying transcutaneous electrical impulses at a second frequency different than the first frequency, the transcutaneous electrical impulses provided at the first and second frequencies giving rise to a first beat impulse having a first interference frequency; and a third electrode supplying transcutaneous electrical impulses at a third frequency and a fourth electrode supplying transcutaneous electrical impulses at a fourth frequency different than the third frequency, the transcutaneous electrical impulses provided at the third and fourth frequencies giving rise to a second beat impulse having a second interference frequency.

15. The interferential current system of claim 1 wherein said controller transmits data via the Internet or other mechanism to remote or off site locations.

* * * * *